United States Patent
Inoue et al.

(10) Patent No.: US 7,937,141 B1
(45) Date of Patent: May 3, 2011

(54) DEVICE FOR IONTOPHORESIS

(75) Inventors: Kazutaka Inoue, Tsukuba (JP); Hirotoshi Adachi, Tsukuba (JP)

(73) Assignee: Hisamitsu Pharmaceutical Co., Inc., Tsukuba-shi (JP)

( * ) Notice: Subject to any disclaimer, the term of this patent is extended or adjusted under 35 U.S.C. 154(b) by 0 days.

(21) Appl. No.: 09/958,113

(22) PCT Filed: Apr. 6, 2000

(86) PCT No.: PCT/JP00/02235
§ 371 (c)(1), (2), (4) Date: Oct. 3, 2001

(87) PCT Pub. No.: WO00/61219
PCT Pub. Date: Oct. 19, 2000

(30) Foreign Application Priority Data

Apr. 12, 1999 (JP) .................................. 11/104639

(51) Int. Cl.
*A61N 1/30* (2006.01)
(52) U.S. Cl. .................................................. 604/20
(58) Field of Classification Search .................... 604/20, 604/19, 21, 22; 601/2–3; 607/149–152
See application file for complete search history.

(56) References Cited

U.S. PATENT DOCUMENTS

| 4,931,046 A | * | 6/1990 | Newman | 604/20 |
| 5,667,487 A | * | 9/1997 | Henley | 604/20 |
| 5,804,957 A | | 9/1998 | Coln | |

* cited by examiner

*Primary Examiner* — Manuel Mendez
(74) *Attorney, Agent, or Firm* — Townsend & Banta

(57) ABSTRACT

A device for iontophoresis that reduces irritation at the beginning of energization and efficiently supplies an amount of current required for drug administration in a predetermined length of time, is provided. With the device for iontophoresis, the oscillation frequency and duty cycle of a transistor 15 are adjusted at the beginning of energization, thereby controlling a back electromotive force developed across a coil 13 to gradually increase the output voltage. The microcomputer 12 controls the transistor 15 so as to receive signals from an output voltage detecting circuit that is formed of resistors 23 and 24 and an output current detecting circuit that is formed of resistors 25 and 26 and a capacitor 27, preventing an increasing of the output voltage when the detected output current reaches a limiting value, and preventing an increasing of the output current when the detected output voltage reaches a limiting value.

11 Claims, 3 Drawing Sheets

DEVICE FOR IONTOPHORESIS

TECHNICAL FIELD

The present invention relates to a device for iontophoresis that is applied to a transdermal or a transmucosal, and more particularly to a device for iontophoresis that reduces irritation at initial electrical energization and supplies a current required for administering a drug to a subject in a predetermined length of time.

BACKGROUND ART

Iontophoresis is a percutaneous absorption promoting system using electricity to externally stimulate a subject. Iontophoresis is based on the principle that forces act on charged molecules such that positively charged molecules migrate from an anode to a cathode and negatively charged molecules migrate from the cathode to the anode in an electric field developed between the anode and cathode when a subject is electrically energized, thereby accelerating the delivery of drug molecules through skin barrier. (Refer to "Journal of controlled release," Vol. 18, 1992, pp. 213-220; "Advanced Drug Delivery Review," Vol. 9, 1992, p. 119; and "Pharmaceutical Research," Vol. 3, 1986, pp. 318-326).

As mentioned above, iontophoresis causes a current to flow between an anode and a cathode, thereby prompting a drug to migrate. In recent years, a constant current apparatus is used which maintains a constant current irrespective of differences in impedance from person to person. Because there is a correlation between the delivery speed of a drug and the amount of current, a constant current apparatus is capable of delivering a drug at a constant speed regardless of the impedance of a subject. As to irritation to the skin of a subject, a current density of about 0.2 mA/cm$^2$ or less is considered low irritation. Safety is ensured by setting a current equal to or less than a value determined from the area of a preparation attached to the skin and a maximum current density (area of preparation× maximum current density≧the amount of current).

However, skin impedance varies from 100 kΩ to near 1 kΩ depending on the time length of hydration time, the time length of energization, the magnitude of current supplied, and location of the subject. If a skin has an impedance of 100 kΩ, a current of 1 mA means an application of a voltage of 100V to the skin, giving a very strong irritation to the subject. This irritation resulting from energization appears prominently at the initial energization, and may cause irritation that the subject cannot stand, even if the voltage and current are within normal ranges.

It is well known that abrupt supply of current at an initial energization causes strong irritation even though the magnitude of current is equal to or less than the aforementioned current density. A variety of measures have been proposed in order to reduce irritation of the skin. For example, Japanese Patent Laid-Open No. 5-49702 discloses an iontophoresis apparatus equipped with current adjusting means that causes a gradual change of current at the beginning of energization. Japanese Patent Laid-Open No. 5-245214 discloses an ion administering system in which constant voltage supplying means is used at the beginning of energization of a subject's body, and then constant current supplying means is used when the current reaches a predetermined value.

These prior art are intended to reduce uncomfortable irritation at the beginning of energization and supply a constant current for drug administration. Even if the current is set to a low current, the apparatus that uses current adjusting means at the beginning of energization as described as above may impress an intolerably high voltage on a subject, if a subject has a very high skin impedance at the beginning of energization. The system that switches from the constant voltage means to the constant current means may cause similar irritation if a constant, sufficiently high voltage is applied, and may require a long time before the current reaches the predetermined value if a constant, very low voltage is applied. Thus, a sufficient measure has not been taken in order to eliminate uncomfortable irritation and to promote highly efficient drug administration.

If a current is adjusted by allowing a sufficient margin against application of a high voltage at the beginning of energization, or a constant voltage is set to a sufficient low value at the beginning of energization, then it takes a longer time before a predetermined current is reached. Therefore, there may be a possibility that during the excess time, the effective blood concentration of drug cannot be attained despite the fact that drug is actually being administered.

DISCLOSURE OF THE INVENTION

Thus, an object of the invention is to provide a device for iontophoresis that reduces irritation at the beginning of energization and effectively supplies an amount of current required for drug administration in a predetermined length of time.

The inventors of the present invention concentrated great attention on achievement of the aforementioned object, and found that a desired amount of drug can be delivered to an intended part of subject's body in a short time without giving an unusual feeling to the subject. This can be done by setting limiting values of the output voltage and output current at the beginning of energization and by gradually increasing these limits from low values to predetermined values. As a result, the inventors made the present invention.

The device for iontophoresis according to the present invention comprises energizing means for causing an output voltage and an output current to gradually increase at the beginning of energization, and output controlling means for causing limiting values of the output voltage and the output current to gradually increase from low values at a beginning of energization, preventing an increasing of the output voltage generated by said energizing means when the detected output current reaches the limiting value, and preventing an increasing of the output current generated by said energizing means when the detected output voltage reaches the limiting value.

The limiting values of the output voltage and output current at the beginning of energization may be set in the respective steps. At least one of a time period of each step and a rate of increase in the limiting value is varied in accordance with elapse of time, thereby optimizing initial energization at a part of a subject's body to which iontophoresis is applied. If there is no limit in the length of time during which iontophoresis is applied to the subject, the standby period (hydration time) may be included in a period from power-on of the device to starting of the output.

In order to accurately control the time period (energization time) for drug administration, the energizing means is controlled by a timer that is driven by a source signal of a quartz crystal unit, a crystal oscillator, or a ceramic resonator. This is because a large error of the timer that determines energization time is detrimental to stable drug administration. The device according to the present invention further includes total-current controlling means for adjusting a total current substantially to a prescribed value, the total-current controlling means being outputted by the energizing means. The output controlling means may be formed of a microcomputer having an A/D converter built therein.

As mentioned above, the present invention is such that the limiting value of the output voltage at the beginning of energization is increased gradually from a low value while at the same time gradually increasing the limiting value of the output current at the beginning of energization from a low value. When either the output voltage or output current reaches its limiting value, the output is prevented from further increasing, the limiting value being increased to a next higher value until a predetermined value is reached. This reduces irritation at the beginning of energization and allows the output current to reach the predetermined value in a short time. The present invention is generally applicable to the skin, but may also be applicable to the mucous membrane.

BEST MODE FOR CARRYING OUT THE INVENTION

The device for iontophoresis according to the present invention will be described in detail with reference to the accompanying drawings.

Figure 2:
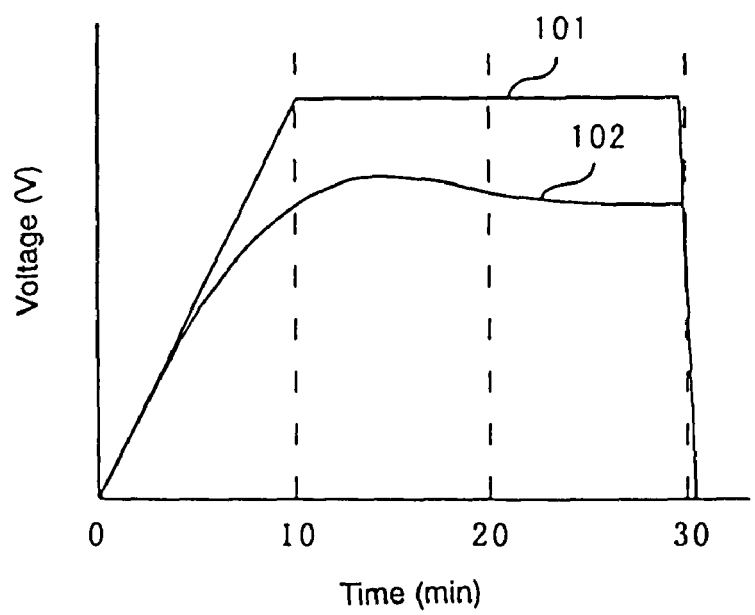
FIG. 2 illustrates examples of a limiting value and measured values of an output voltage when the output is controlled by the limiting value of an output current.
Figure 3:
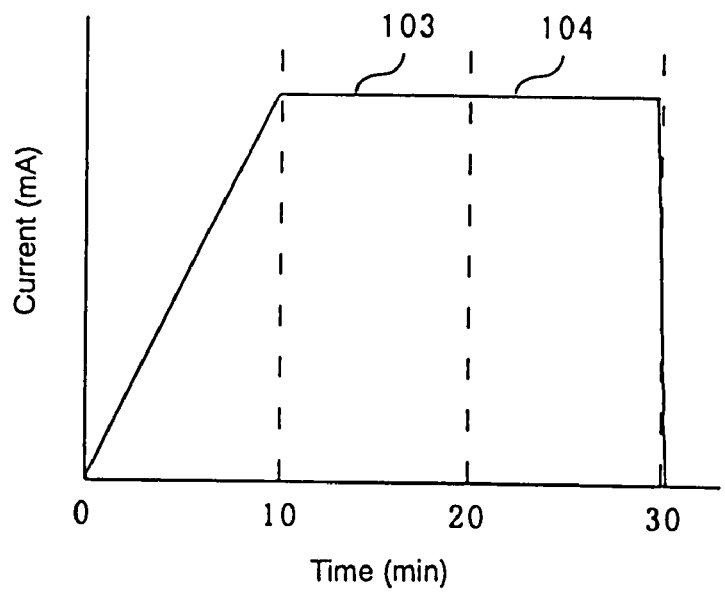
FIG. 3 illustrates examples of a limiting value and measured values of the output current when the output is controlled by the limiting value of the output current.
Figure 4:
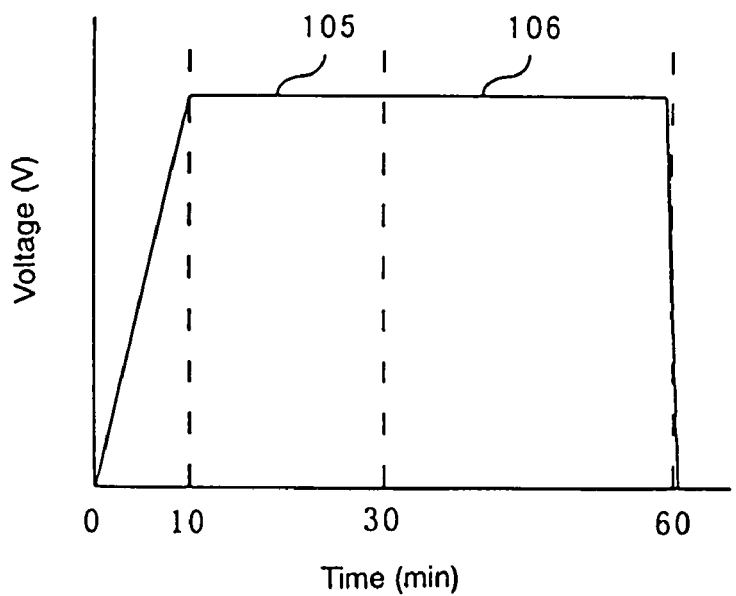
FIG. 4 illustrates examples of the limiting value and measured values of the output voltage when the output is controlled by the limiting value of the output voltage.
Figure 5:
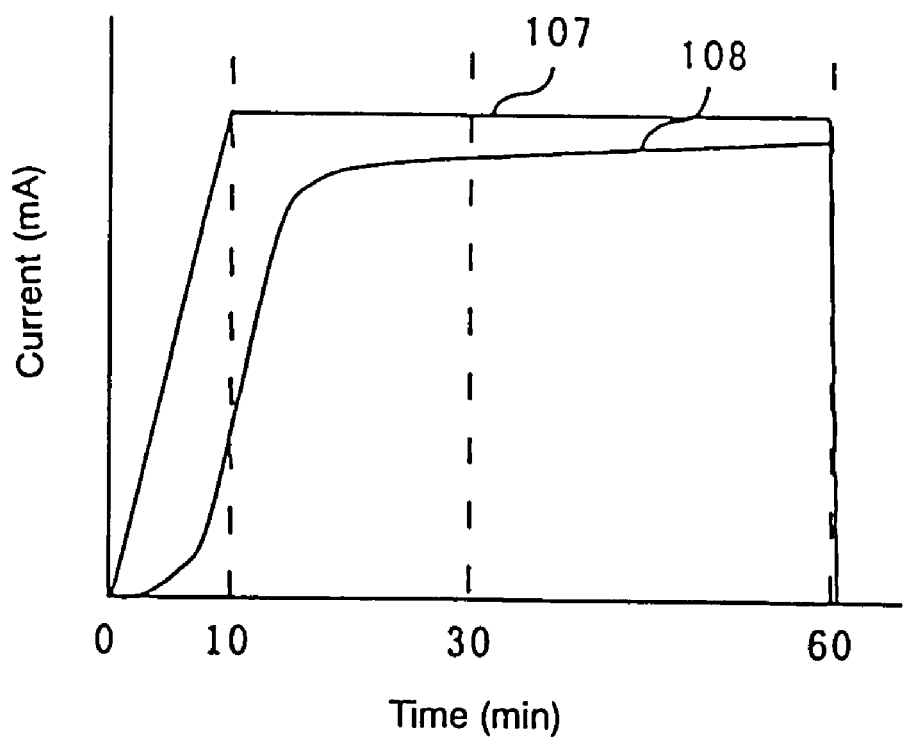
FIG. 5 illustrates examples of the limiting value and measured values of the output current when the output is controlled by the limiting value of the output voltage.

First, a description will be made of the relation between the limiting value and measured values of output voltage and output current of the present device. FIG. 2 illustrates examples of the limiting value 101 and measured value 102 of the output voltage when the output is controlled using the limiting value of the output current. FIG. 3 illustrates examples of the limiting value 103 and measured value 104 of the output current when the output is controlled using the limiting value of the output current. FIG. 4 illustrates examples of the limiting value 105 and measured value 106 of the output voltage when the output is controlled using the limiting value of the output voltage. FIG. 5 illustrates examples of the limiting value 107 and measured value 108 of the output current when the output is controlled using the limiting value of the output voltage. The respective figure plots time (minute) as the abscissa and output voltage (v) or output current (mA) as the ordinate.

In the present invention, the limiting values of the output voltage and output current are increased gradually, as shown in FIGS. 2-5, from a low limiting value at the beginning of energization, according to a predetermined output pattern. When the limiting value reaches a predetermined value, the limiting value is maintained at that value.

When the skin impedance of a subject is equal to or less than a predetermined level (within a range of general applicability), the output controlling means operates in a current control mode. In other words, the output current is equal to the limiting value of output current as shown in FIG. 3, and the output voltage is equal to or less than the limiting value of the output voltage as shown in FIG. 2. When the skin impedance of a subject is higher than the certain value, the output controlling means operates in a voltage control mode. In other words, the output voltage is equal to the limiting value of output voltage as shown in FIG. 4, and the output current is equal to or less than the limiting value of the output current as shown in FIG. 5.

In addition, when the limiting value is being increased in increments, if the output current increases at a lower rate than the output voltage, the output control means may be switched from the current control mode to the voltage control mode. Conversely, when the limiting value is being increased in increments, if the impedance decreases abruptly due to hydration, the output control means is switched from the voltage control mode to the current control mode even though the impedance of the skin of the subject is high at the beginning of energization.

As described above, when the output control means according to the present invention is operating in the current control, the output control means controls the output voltage to prevent a non-tolerable output voltage from being impressed on the skin of a subject if the skin impedance is higher than a predetermined value. When the output control means is operating in the voltage control, the output control means increases the limiting value of the output current gradually to prevent the output current from increasing abruptly if the skin impedance of the subject is lower than a predetermined value. In this manner, the output voltage is gradually increased from a lower value, at which the subject does not feel irritation, to a higher value, thereby prompting hydration of the skin to solve the problem that when the skin impedance is higher than a predetermined value, the output current does not increase promptly to a predetermined value. Controlling the output in this manner allows the output current to reach a predetermined value in a short time for the beginning of energization while a subject feels less irritation.

According to the present invention, in order for the output voltage or the output current to reach a predetermined level in a short time without causing irritation, the output controlling means provides limiting values set for the respective steps and the predetermined value which is a final value of the limiting values. The following procedures may be possible for setting the limiting values.

(1) The predetermined values of the output voltage and the output current are divided into parts of equal value, respectively. The limiting values of the output voltage and the output current are increased in increments of the respective parts, thereby increasing the limiting value gradually from a low limiting value to the predetermined value.

(2) The predetermined values of the output voltage and the output current are divided into parts of equal value, respectively. The output current is increased in increments of the part every predetermined period. The output voltage is increased in increments of the part, the output voltage being increased every predetermined shorter period earlier and every predetermined longer period later, thereby gradually increasing the output from a low limiting value to the predetermined value.

(3) The predetermined values of the output voltage and the output current are divided into parts of equal value, respectively. The output voltage is increased in increments of the part every predetermined period while the output current is increased in increments of the part, the output being increased every predetermined longer period earlier and every a predetermined shorter period later, thereby gradually increasing the output from a low limiting value to the predetermined value.

(4) The predetermined values of the output voltage and the output current are divided into parts of equal value, respectively. The output voltage is increased in increments of the part every predetermined shorter period earlier and then every predetermined longer period later. The output current is increased in increments of the part every predetermined long period earlier and every predetermined short period later, thereby gradually increasing the output from a low limiting value to the predetermined value.

(5) The limiting value of the output current is increased every predetermined period in increments of a relatively small value earlier and then an increasingly large value later, and the limiting value of the output voltage is increased every predetermined period in increments of a relatively large value earlier and then in increments of an increasingly small value later, thereby gradually increasing the output from a low limiting value to the predetermined value.

The device for iontophoresis according to the present invention is particularly useful when an amount of drug administered through iontophoresis must be strictly controlled. For example, the present invention is safely applied for administering a drug such as insulin that has only limited range of tolerable effective blood concentration and concentration at which an adverse reaction occurs. For other drugs having a relatively wide tolerable range of effective blood concentration and concentration at which an adverse reaction occurs, it is important to minimize as many electrical error factors as possible in order to ensure high safety and effectiveness of drugs.

The other drugs used are as follows. As an antibiotic, for example, gentamicin sulfate, sisomicin sulfate (SISO), tetracycline hydrochloride, ampicillin, cefalothin sodium, cefotiam hydrochloride, cefazoline sodium (CEM), etc. may be used.

As an antifungal, amorolfine hydrochloride, croconazole hydrochloride, etc. may be used. As a hypolipemic agent, for example, atorvastatin, cerivastatin, pravastain sodium, simvastacin, etc. may be used.

As a cardiovascular preparation, for example, dlapril hydrochloride, etc. may be used. As an anti-platelet agent, for example, ticlopidine hydrochloride, cilostazol, aspirin, etc. may be used.

As an anti-tumor agent, for example, bleomycin hydrochloride, actinomycin D, mitomycin C, fluorouracil, etc. may be used.

As Antipyretic, analgesic, and antiinflammatory agents, for example, ketoprofen, flurbiprofen, felbinac, indomethacin sodium, diclofenac sodium, loxoprofen sodium, buprenorphinine hydrochloride, eptazocine hydrobromide, pentazocine, butorphanol tartrate, tramodl hydrochloride, morphine hydrochloride, morphine sulfate, fentanyl citrate, fentanyl, etc. may be used.

As an antitussive and expectorant agent, for example, ephedrine hydrochloride, codeine phosphate, etc. may be used. As a tranquilizer, for example, chlorpromazine hydrochloride, atropine sulfate, etc. may be used.

As a Muscle relaxant, for example, ranprisone hydrochloride, eprisone hydrochloride, tubocuraine chloride, ranpesoline hydrochloride, eprisone hydrochloride, etc. may be used. As an antiepileptic drug, for example, clonazepam, zonisamide, phenytoin sodium, ethosuximide, etc. may be used.

As an antumor agent, for example, metoclopramide, etc. may be used. As an antiviral agent, for example, trazodone hydrochloride, imipramine hydrochloride, etc. may be used.

As an antiallergic agent, for example, centirizin dihydrochloride, olopatadine hydrochloride, ketotifen fumarate, azelastine hydrochloride, etc. may be used. As an antiarrhythmic agent, for example, diltiazem hydrochloride, and propranolol hydrochloride, etc. may be used.

As a vasodilator, for example, tolazoline hydrochloride, etc. may be used. As a hypotensive diuretic, for example, metlazone, etc. may be used.

As a therapeutic agent for treating diabetes, for example, pioglitazone hydrochloride, mexiletine hydrochloride, glibenclamide, metformin hydrochloride, etc. may be used.

As an anticoagulant, for example, sodium citrate, etc. may be used. As a hemostatic drug, for example, metetrenone, tranexamic acid, etc. may be used.

As an antituberculous agent, for example, isoniazid, ethanbutol hydrochloride, etc. may be used. As a hormone preparation, for example, estradiol, testosterone, prednisolone acetate, dexamethasone sodium phosphate, etc. may be used.

As a narcotic antagonist, for example, levallorphan tartrate, naloxone hydrochloride, etc. may be used.

Embodiment

Figure 1:
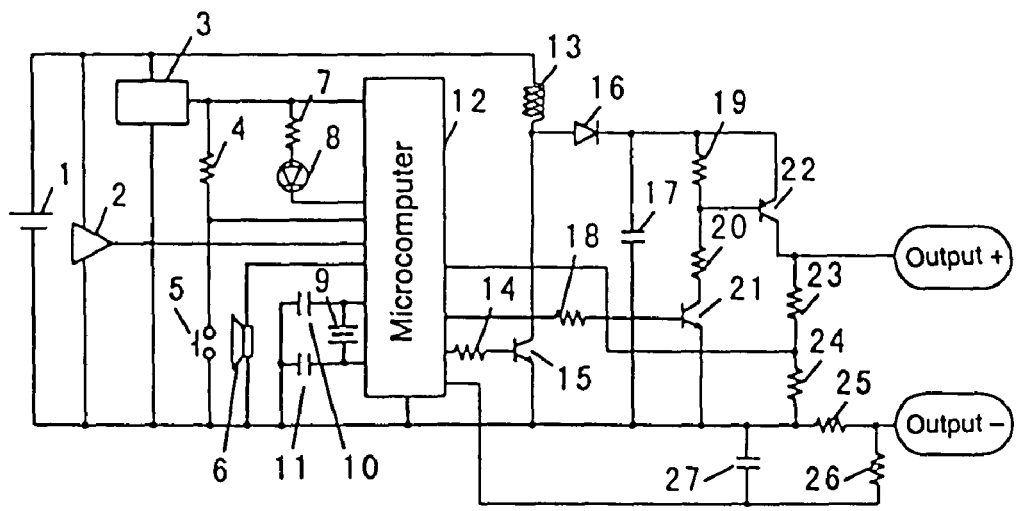
FIG. 1 illustrates an embodiment of a device for iontophoresis according to the present invention.

FIG. 1 illustrates an embodiment of a device for iontophoresis according to the present invention. The device has output controlling means that supplies an output with less irritation to a subject in a short time, and highly accurate timer means.

Referring to FIG. 1, a battery 1 is a battery such as a primary/secondary battery of a coin type. A power supply monitor IC 2 is used to monitor the voltage of the battery 1. When the battery voltage drops below a predetermined value, the power supply monitor IC 2 warns a microcomputer 12 of the voltage drop of the battery 1. A switch 5 is used to turn on or off the present device and connected to a resistor 4, the connecting point of them being connected to the microcomputer 12. A three-terminal regulator 3 is used to smooth out the voltage supplied to the microcomputer 12. The three-terminal regulator 3 has a low voltage drop and a setting voltage that is below a detection voltage of a power supply monitor IC 2 by 0.3 V to 1.0 V and more, is recommended.

A buzzer 6 is used to sound, thereby indicating to the outside, for example, the power-on and completion of energization. An LED (light-emitting diode) 8 is connected in series with a resistor 7 and indicates to the outside the operating status of the device, flashing slowly when the timer is operating but energization is not being performed, flashing rapidly when the timer is operating and energization is being performed, and going off when the circuit is not operating. A ceramic resonator 9 connected to capacitors 10 and 11 is used to generate a system clock (source signal) of the microcomputer 12. The generated frequency is properly determined according to the current consumption and operating speed.

A coil 13, a transistor 15, a diode 16, a capacitor 17, and a resistor 14 are components that form a booster circuit that provides a boosted-voltage from the battery voltage. The microcomputer 12 outputs a signal through the resistor 14 to cause the transistor 15 to perform a switching operation to generate a back electromotive force across the coil 13, which in turn is rectified by the diode 16 to be stored in the capacitor 17. When the transistor 22 conducts, the charge stored in the capacitor 17 is supplied to the output terminal. The microcomputer 12 provide a signal through the resistor 18 to the transistor 21 to make the transistor 21 to conduct. These circuits form the energizing means of the present invention that causes the output voltage and output current to gradually increase at the beginning of energization that resides in the program built in the microcomputer 12.

Resistors 23 and 24 form an output voltage detecting circuit that divides the output voltage and sends the divided voltage to an A/D converter (a circuit that converts an analog signal into a digital value) in the microcomputer 12. Resistors 25 and 26 and a capacitor 27 form an output current detecting circuit in which the resistor 25 converts the current into a voltage which in turn is smoothed out by the resistor 26 and the capacitor 27, and then sent to the A/D converter in the microcomputer 12. The microcomputer 12 has the function of the output controlling means of the present invention to cause the limiting values of the output voltage and the output current to increase gradually from low values to predetermined values at the beginning of energization. When the output current detected by the output current detecting circuit reaches the predetermined limiting value, the output controlling means prevents the increasing of the output voltage of the energizing means. When the output voltage detected by the output voltage detecting circuit reaches the predetermined limiting value, the output controlling means prevents the increasing of the output current of the energizing means.

The basic operation of the present invention will be described. When the switch 5 is depressed, the microcomputer 12 starts. The microcomputer 12 checks a signal from the power supply monitor IC 2 to determine whether the power supply voltage is equal to or higher than a predetermined value. If the power supply voltage is equal to or higher than the predetermined value, then the microcomputer causes the buzzer 6 and the LED 8 to indicate to the user that the circuit has been activated. Then, the timer starts to operate and generates outputs under the program.

At the beginning of energization, the oscillation frequency and duty cycle of the transistor 15 are adjusted to control the back electromotive force generated across the coil 13, thereby increasing the output voltage gradually. The output may be set as follows: for example, the oscillation frequency of the transistor 15 is fixed and the initial duty cycle of the output is set to 5%. The duty cycle is increased by 5% every predetermined period, so that the output voltage can be changed in ten steps up to a duty cycle of 50%.

At the same time, the microcomputer 12 performs A/D conversion of the signal from the output current detecting circuit to detect the output current. If the output current has reached a limiting value, the microcomputer prevents the output voltage from increasing. If the output current has not reached yet, the microcomputer continues to increase the output voltage. The microcomputer 12 causes the limiting value of the output current to gradually increase according to the previously programmed current pattern. In this manner, allowing the output voltage and the output current to be increased simultaneously so that the output is maintained at a value limited by the output current or the output voltage after a predetermined period.

By using an 8-bit A/D converter and a resistor having an error of ±1%, the output current according to the embodiment can be detected with an error of equal to or less than ±5% usually, and equal to or less than ±10% at most. In order to improve the accuracy of the A/D converter, a separate reference voltage may be employed and also an amplifier may be added to the output current detecting circuit.

The output status after a predetermined period in this embodiment is in the constant current control mode as shown in FIGS. 2 and 3 since the output voltage is set to be enough for obtaining the present output current. When the skin impedance is too high, however, the predetermined value of output current may not be attained as shown in FIGS. 4 and 5.

In this case, a total current controlling means may be added in which the current may be detected at all times and the time length for energization is extended according to the detected current.

The source signal for the timer according to the present embodiment is based on the ceramic resonator and therefore the accuracy of the timer does not generate errors so as to influence the drug administration. Desirable elements other than ceramic resonator are, for example, a quartz crystal unit and a crystal oscillator. The feature of these elements is that they offer high frequency accuracy (100 ppm or less) as opposed to a CR oscillator (oscillator based on resistors and capacitors). For the device according to the present invention in which the current requires to be controlled with high frequency accuracy, these elements are very useful as a timer component that determines the accuracy of the device.

While an embodiment of the present invention has been described with reference to the drawings, the present invention is not limited to the embodiment but a variety of modifications can be made without departing from the scope of the invention.

INDUSTRIAL APPLICABILITY

According to the present invention, an iontophoresis device can be obtained which reduces irritation at the beginning of energization and provides efficient supply of current required for drug administration within a predetermined time length.

The invention claimed is:
1. A device for iontophoresis comprising:
energizing means for causing an output voltage and an output current to gradually increase at the beginning of energization;
detection means for detecting output current and output voltage; and
output controlling means for establishing and causing limiting values of the output voltage and the output current to gradually increase from low values at a beginning of energization, preventing an increasing of the output voltage generated by said energizing means when the detected output current reaches the limiting value, and preventing an increasing of the output current generated by said energizing means when the detected output voltage reaches the limiting value.
2. The device for iontophoresis according to claim 1, wherein the limiting values of the output voltage and output current at the beginning of energization are set in a stepwise fashion, respectively.
3. The device for iontophoresis according to claim 2, wherein at least one of a time period of each step in the stepwise fashion and a rate of increase in the limiting value, is controlled to change in accordance with elapse of over time.
4. The device for iontophoresis according to claim 1, wherein said energizing means is programmed to perform includes a standby period from power-on of the device to starting of the output of voltage and current.
5. The device for iontophoresis according to claim 1, wherein a period of energization by the energizing means is controlled by a timer that is driven by a source signal of a quartz crystal unit, a crystal oscillator, or ceramic resonator.
6. The device for iontophoresis according to claim 1, further comprising total current controlling means for adjusting a total current substantially to a prescribed value, the total current being outputted by said energizing means.

7. The device for iontophoresis according to claim 1, wherein said output controlling means is formed of a microcomputer having an A/D converter built therein.

8. The device for iontophoresis according to claim 1, wherein the energizing means further comprises a timer driven by a source signal sent by a quartz crystal unit, a crystal oscillator, or a ceramic resonator.

9. A method for iontophoresis comprising:
   (a) establishing limiting values of output voltage and output current during predetermined discrete incremental steps in iontophoretic energization from a beginning of energization to a peak of energization, a final limiting value of output voltage and a final limiting value of output current, via an output controlling means;
   (b) incrementally energizing transdermal and/or transmucosal tissues of a patient at predetermined discrete incremental steps of energization by outputting current and voltage using an energizing means, while detecting the output current and output voltage, via a detection means, during each predetermined discrete incremental step of energization,
   wherein the output controlling means controls the output voltage and output current so as to gradually increase the output voltage and output current from the beginning of energization to a predetermined final limiting value of energization, and the limiting values of the output voltage and the output current are established so as to gradually increase from low values at the beginning of energization to higher values at the final limiting value of energization, thus preventing any increase in output voltage generated by said energizing means when the detected output current reaches the final limiting value thereof, and preventing any increase in output current generated by said energizing means when the detected output voltage reaches the final limiting value thereof.

10. The method of claim 9, wherein said energizing means is programmed to perform a standby period before incrementally energizing transdermal and/or transmucosal tissues of a patient.

11. The method of claim 9, wherein the period of energization by the energizing means is controlled by a timer that is driven by a source signal of a quartz crystal unit, a crystal oscillator, or a ceramic resonator.

\* \* \* \* \*